United States Patent [19]
Pallas et al.

[11] Patent Number: 5,906,962
[45] Date of Patent: *May 25, 1999

[54] NON-AQUEOUS SUSPENSION CONCENTRATES OF HIGHLY WATER-SOLUBLE SOLIDS

[75] Inventors: Norman Robert Pallas, Freehold, N.J.; James L. Hazen, Galloway, Ohio; Robert Jene Riedemann, Neptune; Thomas E. Ruch, Sicklerville, both of N.J.

[73] Assignee: Rhodia Inc., Cranbury, N.J.

[*] Notice: This patent is subject to a terminal disclaimer.

[21] Appl. No.: 08/926,920

[22] Filed: Sep. 10, 1997

Related U.S. Application Data

[63] Continuation-in-part of application No. 08/362,057, Dec. 22, 1994, Pat. No. 5,707,551.

[51] Int. Cl.$^6$ .......................... A01N 25/04; A01N 37/10; A01N 37/18; B01J 13/00
[52] U.S. Cl. ................. 504/116; 71/64.08; 71/DIG. 1; 137/13; 241/16; 504/188; 504/192; 504/206; 504/324; 504/325; 504/337; 516/31; 516/33; 516/909; 516/928; 424/405
[58] Field of Search ..................... 252/308, 309, 252/314, 353, 363.5; 510/418, 421, 427; 137/13; 504/116; 71/DIG. 1, 64.08; 424/405

[56] References Cited

U.S. PATENT DOCUMENTS

| | | | |
|---|---|---|---|
| 2,920,045 | 1/1960 | Hearn et al. | 252/137 |
| 3,089,848 | 5/1963 | Morway | 252/18 |
| 3,594,151 | 7/1971 | Sprayberry et al. | 504/116 |
| 3,882,247 | 5/1975 | Bullock | 424/337 |
| 3,960,742 | 6/1976 | Leonard | 252/90 |
| 3,984,463 | 10/1976 | Pilgram | 260/501.17 |
| 4,183,741 | 1/1980 | West et al. | 71/92 |
| 4,227,911 | 10/1980 | Leonard et al. | 71/77 |
| 4,265,406 | 5/1981 | Palgrave et al. | 241/16 |
| 4,294,633 | 10/1981 | Clay | 149/2 |
| 4,331,490 | 5/1982 | Palgrave et al. | 149/46 |
| 4,372,777 | 2/1983 | LeClair et al. | 71/93 |
| 4,393,151 | 7/1983 | Dawans et al. | 523/130 |
| 4,482,372 | 11/1984 | Palgrave et al. | 71/35 |
| 4,673,526 | 6/1987 | Zabotto et al. | 252/174.16 |
| 4,784,788 | 11/1988 | Lancz | 252/114 |
| 4,824,475 | 4/1989 | Markley et al. | 71/93 |
| 4,876,354 | 10/1989 | Siegel et al. | 548/341 |
| 4,918,085 | 4/1990 | D'Silva et al. | 514/407 |
| 4,943,307 | 7/1990 | Detre et al. | 71/3 |
| 4,950,424 | 8/1990 | van der Hoeven et al. | 252/540 |
| 5,079,370 | 1/1992 | D'Silva et al. | 548/365 |
| 5,082,591 | 1/1992 | Marchetto et al. | 252/351 |
| 5,179,096 | 1/1993 | Gentilini et al. | 514/253 |
| 5,223,524 | 6/1993 | Valcke | 514/383 |
| 5,254,344 | 10/1993 | Dookhith et al. | 71/DIG. 1 |
| 5,290,751 | 3/1994 | Fiard et al. | 504/116 |
| 5,362,312 | 11/1994 | Skaggs et al. | 106/189 |
| 5,468,418 | 11/1995 | Rabone | 252/174.25 |
| 5,707,551 | 1/1998 | Pallas et al. | 252/308 |

*Primary Examiner*—Richard D. Lovering
*Attorney, Agent, or Firm*—John A. Shedden

[57] ABSTRACT

Stable, concentrated non-aqueous suspensions of water-soluble solids are prepared by using a water soluble active compound comprising water hydratable polysaccharides, biocides, fertilizers and mixtures thereof dispersed in water-miscible organic liquid carriers, preferably lower alkadiols in conjunction with a specific three component surfactant system, i.e., a system comprising a nonionic polymeric viscosity modifier surfactant; an anionic surfactant; and a nonionic surfactant having a bulky hydrophobic substituent group.

15 Claims, No Drawings

NON-AQUEOUS SUSPENSION CONCENTRATES OF HIGHLY WATER-SOLUBLE SOLIDS

RELATED APPLICATIONS

This application is a continuation-in-part of U.S. Ser. No. 08/362,057 filed on Dec. 22, 1994 now U.S. Pat. No. 5,707,551.

FIELD OF THE INVENTION

The present invention relates to a method for preparing concentrated suspensions of water-soluble solids with excellent storage stability and the concentrates thus formed. The method comprises suspending the solids in a water-soluble organic liquid such as a low molar mass glycol in the presence of a three component surfactant system.

BACKGROUND OF THE INVENTION

Many handling problems may arise when one is forced to prepare aqueous end-use formulations and/or slurries from solids, especially active solids, e.g. wettable bioactive powders as is often the situation in the agricultural industry. Farmers preparing tank mixes of herbicides, insecticides and/or other bioactives from solids for applications to crop and soil are exposed to certain safety hazards and inconveniences due to the generation of noxious dusts which may be irritable to the skin and hazardous to breathe.

Additionally, finely ground powders, even so-called powders, of many water-soluble bioactives when prepared as tank mixes do not disperse well, they have poor spontaneity or "bloom" and have low suspendability, they have poor re-dispersibility and are incompatible with other bioactives as compared to liquid bioactive concentrates. Thus, final formulators, such as farmers, when preparing diluted aqueous active compositions find that the handling and application of solids materials such as fertilizers, are much facilitated if the material can be supplied in a fluid rather than solid form. Economics then dictates that the active material be supplied in a highly concentrated fluid to the final formulator.

Saturation solubility in water of many water-soluble active constituents, such as ammonium nitrate, is too low to make it economical to supply it to the end-user simply in the form of a solution. Alternatively, highly concentrated suspensions of water soluble compounds, both in water and in organic liquids, have very poor storage, freeze/thaw, and heat/cool stability.

As a result of the spontaneous crystal dissolution-recrystallization process, there occurs a progressive increase in the size of the particulate active material. This increase in particle size results in settling, bleed and changes in viscoelastic properties and thus severely limits concentrate loading levels.

The instant invention concerns a unique formulation which, to a great extent, addresses and overcomes the above problems.

Particle size stability of water-soluble particulate solids is obtained in a twofold manner. First, by appropriate selection of the organic carrier used as the continuous phase, the temperature coefficient of solubility can be controlled, thus stabilizing the particle size of the solids throughout usual commercial storage times and temperature cycles. The major component of the carrier liquid is non-aqueous, although small amounts of water may be used to modify the performance. Secondly, recognizing that a small number of large particles has a smaller total surface area than a large number of small particles regardless of morphology, the surface-free energy of the active solid material is lowered via surfactant adsorption onto the particle surface, thus reducing the necessity to obtain a minimization of the surface area which promotes growth of the particles.

The particle size stability and other desirable characteristics of the concentrate such as low viscosity, minimum syneresis and high bloom are primarily controlled through the use of a three component surfactant system.

The first component, a nonionic viscosity-improver material, preferably a polymeric material and most preferably an ethylene oxide-propylene oxide block copolymer, is primarily used, through rheology control, to create a stable dispersion and secondarily to mollify crystal growth.

The second component, an anionic surfactant, preferably a sulfonate, albeit having a syneresis-increasing influence, is utilized primarily to synergistically reduce the viscosity enhancing effect of the polymeric first component and secondarily, as a result of its affinity for the surface of the solids, to aid in the dispersibility of the solid particles.

The third component, which is a bulky nonionic surfactant containing a large hydrophobic group, preferably an ethoxylated tristyryl phenol such as Soprophor BSU® (Rhône-Poulenc Inc., Cranbury, N.J.), is primarily used to reduce the packing of the particles, i.e., it reduces syneresis or settling and serendipitously enhances the bloom or dispersibility that occurs when the concentrated composition is diluted by pouring it into an aqueous medium to achieve the final concentration of the end-use formulation.

This third component also has a tendency to increase the viscosity of the concentrate.

Optionally, a minor amount of water may be added to the concentrate primarily to assist in adjusting the temperature coefficient of solubility which ultimately minimizes changes in particle size.

U.S. Pat. No. 5,082,591 to Marchetto, et al. discloses emulsifiable concentrated solutions of herbicides, pesticides, and other active agricultural compounds comprising a polyoxyethyleneated/polyoxypropylenated (1-phenylethyl) phenol as the surfactant. The compositions also contain a wetting agent, a stabilizing agent and a second nonionic, cationic, or amphoteric surfactant. The compounds enable agricultural actives to have improved shelf life stability, are stable in water and enable the production of highly concentrated solutions for ease of handling and transport.

U.S. Pat. No. 4,393,151 to Dowans, et al. teaches stabilized suspensions of water soluble polymers in a liquid hydrocarbon medium including a thickening agent consisting of the alkaline earth metal salts of fatty acids having from 6–33 carbon atoms. The suspensions dissolve readily in water and actively disperse. They are allegedly useful in enhanced oil field recovery. U.S. Pat. No. 3,960,742 to Leonard discloses corrosion inhibitor compositions comprised of a ethylene glycol monoalkyl ether solvent, inorganic alkaline solids dispersed therein and small amounts of two or more surfactants as suspension agents. The compositions are highly concentrated yet shelf stable and very effective in the removal of grease, oil, tar, asphalt, etc. from all surfaces. The concentrate is also non-flammable, ecologically benign and relatively non-toxic.

U.S. Pat. No. 4,265,406 to Palgrave, et al. discloses the use of an additive such as a polysaccharide to at least partially inhibit regrowth at crystal surfaces when comminuting concentrated solid materials such as water soluble explosives or fertilizer salts in saturated solutions.

Through use of the organic carrier and surfactant systems of this invention, exceptionally high loadings, i.e., from about 40 to 85% by weight of the total weight of the composition, of suspensions of water-soluble solids are prepared which exhibit minimal changes in particle size and are characterized by settling and visco-elastic properties that produce suspensions which are extremely stable even under long term storage conditions.

SUMMARY OF THE INVENTION

Stable, concentrated non-aqueous suspensions of water-soluble solids are prepared by using a water soluble active compound comprising water hydratable polysaccharides, biocides, fertilizers and mixtures thereof dispersed in water-miscible organic liquid carriers, preferably lower alkadiols in conjunction with a specific three component surfactant system, i.e., a system comprising a nonionic polymeric viscosity modifier surfactant; an anionic surfactant; and a nonionic surfactant having a bulky hydrophobic substituent group.

DETAILED DESCRIPTION OF THE INVENTION

The formulations of the instant invention are eminently suitable for suspending solids of any water-soluble material that exist as a separate solid phase in the fully formulated concentrate. Many such materials find application in the explosive and agricultural areas, especially in the fertilizer and pesticide formulations. Examples of such water-soluble materials include salts such as potassium nitrate, ammonium dihydrogen phosphate, ammonium nitrate, sodium nitrate, calcium nitrate, potassium chloride, sodium chloride, ammonium phosphate, ammonium polyphosphate, potassium hydrogen phosphate, disodium hydrogen phosphate and the like, and non-salt-like compounds such as urea. Pesticides, adjuvants and other agricultural use materials such as boric acid, butocarboxime, acephate, dimethoate, dimehypo, vamidothion, and methomyl; herbicides such as dalapon (2,2 dichloropropirionic acid, sodium salt) ammonium sulfamate, dicamba, cacodylic acid, foamesafen, and glyphosate; and fungicides such as copper sulfate, fosetyl-Al (aluminum tris (O-ethyl phosphonate), benalaxyl, guazatine, and kasugamycin and water hydratable gums such as xanthan, guar, acacia, whelan and gum derivatives, are also useful as active water soluble compounds in the practice of the present invention.

The term "water-soluble" is used herein as meaning any material having a solubility in water of greater than one (1) weight percent (wt. %) based on the total weight of the material and water at 24° C.

The concentration or loading of the solid material in the formulations of this invention can be from 5.0 to 85 wt. % preferably from 15–80 wt. %; and most preferably from 20–60 wt. % based on the total weight of the concentrate.

The average diameter particle size of the water-soluble solid material can be from 0.5 to 500 microns; preferably from 30 to 200 microns; most preferably from about 80 to about 120 microns.

The superior stability and visco-elastic properties of the non-aqueous suspension concentrates of the present invention are derived from the particle/particle and particle/carrier phase interactions dictated by the selection of the carrier phase.

Water hydratable compounds are those particles defined as having the ability to absorb water and swell in a generally aqueous medium. Preferably, the water hydratable compounds are polysaccharides and more specifically, the polygalactomannans such as guar gum, xanthan gum, acacia gum, whelan gum, gum arabic, and the derivatives thereof. Suitable derivatives of the gums include hydroxypropyl ethers, methyl ethers, carboxymethyl ethers and the like. These polygalactomannan derivatives are the preferred water hydratable compounds useful in the practice of the present invention, the most preferred being hydroxypropyl guar, hydroxypropyl xanthan gum, and hydroxypropyl whelan gum.

The water hydratable compound comprises from about 5.0 wt. % to about 50 wt. % of the suspension concentrate. Preferably, the polysaccharide is incorporated in amounts of from about 10 wt. % to about 45 wt. % and most preferably in an amount of from about 15 wt. % to about 30 wt. %. The use of these compounds results in a water soluble, non-aqueous suspension comprised of both a continuous and discontinuous phase.

The carrier can be any water-miscible low molecular weight organic fluid which is liquid at room temperature. The term "water-miscible" means that the organic liquids are miscible with water in all proportions, i.e., they will form a single phase with the water.

Where the water-soluble solids are bioactive, it is preferred that the carrier be inert or at least acceptable for the intended end-use of the diluted concentrate. For example, if the solids are pesticidally active, the carrier should be agronomically acceptable.

All water-miscible organic liquid carriers do not work with equal effectiveness and it is generally preferred that the organic liquid has an hydroxide functionality and relatively low molecular weight; thus mono- or poly-functional lower alcohols are particularly effective as well as their ethers or esters. Among these are the lower alkanols and alkadiols. Maximum water miscibility is obtained with $C_1$–$C_4$ alcohols (methanol, ethanol, isopropyl alcohol, etc.). Of the glycols (alkadiols, alkatriols, etc., e.g., ethylene glycol and propylene glycol) diethylene glycol is particularly preferred.

The carriers of this invention also include water-miscible ketones, such as acetone, methyl ethyl ketone, methyl isobutyl ketone, cyclohexanone, and ethers. Water-soluble or strongly polar solvents such as formamide, dimethyl formamide, dimethyl sulfoxide, or N-methyl pyrrolidone and the like are acceptable. Partially miscible liquids such as furfuryl, furfuryl alcohol and alkoxylates are also useful as carriers in this invention. Mixtures of different liquids are often suitable.

Most preferably, the carrier is a low molecular weight glycol with a molecular weight≦5000 dal., i.e. a molar mass≦5000. The compounds that exhibit the best results include triethylene glycol, polyethylene glycol, liquid tall oil fatty acid (TOFA) and liquid tall oil fatty acid ethoxylate, all of which may further include an excipient such as citric acid to promote hydration with those compounds capable of being hydrated.

The carrier concentration in the suspension concentrate should be from about 10 to 90 wt. % based on the total weight of the concentrate; preferably from about 40 to 80 wt. % and most preferably from about 45 to 70 wt. %.

The stabilizing properties of the concentrated water-soluble solids/carrier compositions are achieved primarily through the use of a multi-component surfactant system which is from 4 to 15 wt. % of the total weight of the concentrate.

The first component, which is a nonionic viscosity-modifier, preferably a polymeric material with a molar mass of less than 15,000, is used to control the rheology of the concentrate and thereby primarily creates a stable dispersion and secondarily mollifies the crystal growth of the solids particles.

Examples of acceptable nonionic viscosity improvers are the polyacrylic acids and their sodium salts; the polyglycol ethers of fatty alcohols and polyethylene oxide or polypropylene oxide condensation products and mixtures thereof and include ethoxylated alkyl phenols (also designated in the art as alkylaryl polyether alcohols); ethoxylated aliphatic alcohols (or alkyl polyether alcohols); ethoxylated fatty acids (or polyoxyethylene fatty acid esters); ethoxylated anhydrosorbitol esters (or polyethylene sorbitan fatty acid esters), long chain amine and cyclic amine oxides which are nonionic in basic solutions; long chain tertiary phosphine oxides; and long chain dialkyl sulfoxides.

Preferably the nonionic viscosity improvers are polymeric such as ethoxylated polyoxypropylene glycols (polyalkylene oxide block copolymers): ethoxylated polyoxypropylene monohydric alcohols (polyalkylene oxide blocks copolymers of monohydric alcohols); and ethoxylated polyoxypropylene alkyl phenols (polyalkylene oxide block copolymers of alkyl phenols).

Most preferably the viscosity improvers are ethylene oxide-propylene oxide block copolymers of the formula:

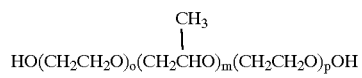

wherein o and p denotes the number of moles of ethylene oxide; i. e., in the range wherein o is a whole number from about 2 to 128 and p is from about 2 to 128 and m is moles of propylene oxide in the range of from about 16 to 67.

The viscosity modifier is present in the concentrate in an amount of from about 2 to 20 wt. %; preferably from about 2 to 7 wt. %; and most preferably from about 2 to 6 wt. %; said percentage based on the total weight of the concentrate.

The second component of the surfactant stabilizer system is an anionic surfactant whose primary function is to synergistically control the viscosity increase caused by the crystal growth inhibiting first component. Secondarily, its affinity for adhesion to the surface of the particulate solids aids in the dispersibility of the particles about the target substrate.

Anionic surfactants useful herein include alkyl and alkyl ether sulfates. These materials have the respective formulae $ROSO_3M$ and $RO(C_2H_4O)_x SO_3M$ wherein R is an alkyl, alkenyl or alkylaryl group of about 8 to about 22 carbon atoms, x is 1 to 10, preferably 1 to 4, and M is a water-soluble cation such as ammonium, sodium, potassium, magnesium, triethanolamine (TEA), etc. The alkyl ether sulfates useful in the present invention are condensation products of ethylene oxide and monohydric alcohols having from about 8 to about 22 carbon atoms. Specific examples of the above sulfates include ammonium lauryl sulfate, magnesium lauryl sulfate, sodium 2-ethyl-hexyl sulfate, sodium octyl sulfate, sodium oleyl sulfate, sodium tridecyl sulfate, triethanolamine lauryl sulfate, ammonium linear alcohol, ether sulfate, ammonium nonylphenol ether sulfate, and ammonium nonoxynol-4-sulfate.

Another suitable class of anionic surfactants are the water-soluble salts of the general formula:

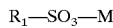

wherein $R_1$ is selected from the group consisting of:
i) a straight or branched chain, saturated aliphatic hydrocarbon radical having from about 8 to 24, preferably 12 to 18 carbon atoms;

ii) a mono-, di-, or tri- $C_{1-C6}$ alkyl substituted aryl wherein the aryl is preferably a phenyl or naphthyl group;

iii) alpha-olefins having from about 12 to 24 carbon atoms, preferably 14 to 16 straight chain carbon atoms, most preferably 1-dodecene, 1-tetradecene, 1-hexadecene, 1-octadecene, 1-eicosene, and 1-tetracosene; and iv) naphthalene-formaldehyde condensation products.

Additional examples of anionic synthetic surfactants which are useful in the practice of the present invention are: i) the isethionates, i.e. the reaction products of fatty acids esterified with isethionic acid and neutralized with sodium hydroxide where, for example, the fatty acids are derived from coconut oil; and ii) the n-methyl taurates, i.e., the sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278 which are hereby incorporated by reference.

Still other anionic synthetic surfactants include the classes designated as the sulfosuccinates and sulfosuccinamates. These are of the general formulae:

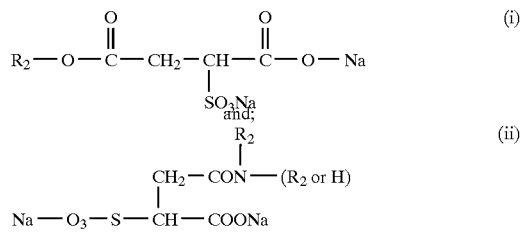

respectively, wherein $R_2$ is a $C_2$–$C_{20}$ alkyl or alkylamide.

These classes include such surface active agents as disodium N-octadecylsulfo-succinamate; tetrasodium N-(1,2-dicarboxyethyl)-N-octadecylsulfo-succinamate; diamyl ester of sodium sulfosuccinic acid; dihexyl ester of sodium sulfosuccinic acid; and dioctyl esters of sodium sulfosuccinic acid.

Another class of anionic organic surfactants are the β-alkyloxy alkane sulfonates. These compounds have the following formula:

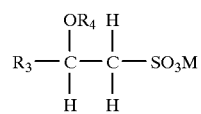

where $R_3$ is a straight chain alkyl group having from about 6 to 20 carbon atoms, $R_4$ is a lower alkyl group having from about 1 to 3 carbon atoms, and M is a water-soluble cation as hereinbefore described.

Specific examples of β-alkyloxy-alkane-1-sulfonates, or alternatively 2-alkyloxy-alkane-1-sulfonates include:

potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium β-methoxyoctadecylsulfonate, and ammonium β-n-propoxydodecylsulfonate.

Also to be included in the anionic class of surfactants useful in the practice of the present application are the disulfonates of the general formula:

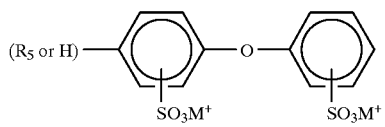

wherein $R_5$ is a $C_8$–$C_{20}$ alkyl group and M is a water-soluble cation as hereinabove described. The preferred anionics of the disulfonate class are disodium dodecyl diphenyloxide disulfonate and ethoxylated nonylphenyl ammonium disulfonate. All of the above-described anionic surfactants and mixtures thereof may or may not be ethoxylated with from about 1 to about 10 ethylene oxide (EO) units per "R" unit.

The anionic surfactant is present in the concentrate in an amount of from about 1.0 to 20 wt. %; preferably from about 1.0 to 7.0 wt. %; and most preferably from about 1.0 to 5.0 wt. %; said percentage based on the total weight of the concentrate.

The third component of the surfactant stabilizer system is a bulky nonionic surfactant containing a large hydrophobic group. These third components are of the formula $R_6O(C_nH_{2n}O)_xR_7$ wherein $R_6$ is selected from the group consisting of a phenyl; a mono-, di- or tri-substituted phenyl; a phenyl $C_1$–$C_6$ alkyl; and a mono-, di-, or tri-substituted phenyl $C_1$–$C_6$ alkyl wherein the phenyl substituent group(s) each have a total of about 1 to 30 carbon atoms, and wherein each substitution can be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; wherein $R_7$ is a hydrogen, phosphate or sulfate entity; and wherein x is a whole number of from about 2 to 100. Preferably this component is a dinonyl phenol or a tristyrylphenol, most preferably an ethoxylated dinonyl phenol or tristyrylphenol and/or any esters thereof. These ethoxylated tristyrylphenols and their derivatives can be described as comprising at least one poly-oxyethyleneated and/or oxypropyleneated poly (1-phenyethyl) phenol or phenyl ester of the formula:

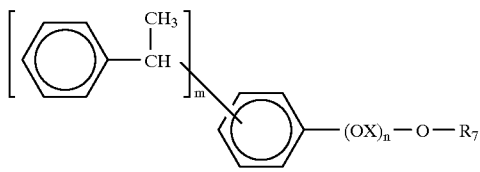

wherein m is 2 or 3; (OX) is a recurring oxyethyleneated and/or oxy-propyleneated unit;

n is a whole number of from about 8 to 35; preferably from about 16 to 30; and $R_7$ is a hydrogen, phosphate or sulfate entity.

The bulky nonionic surfactant is present in the concentrate in an amount of from 1.0 to 20 wt. %; preferably from about 1.0 to 7.0 wt. %; and most preferably from about 1.0 to 5.0 wt. %; said percentage based on the total weight of the concentrate.

Water can optionally be added to the concentrate in an amount of from 0 to 30 wt. %. The water acts primarily to control the temperature coefficient of solubility and thus helps to minimize particle size changes. Preferably, the is water is added in an amount from about 0 to 20 wt. %; and most preferably, in an amount from about 0 to 8.0 wt. %; said water percentages being based on the total weight of the concentrate.

Although the method of preparing the concentrates of this invention is not critical, a preferred approach is to first prepare a mixture of the nonionic surfactant with the bulky hydrophobic group, then add the anionic surfactant, the organic liquid carrier, and the water (if any) and load this mixture into a mill. The nonionic polymeric viscosity improver is then milled into the mixture. The solid water-soluble material that is to be concentrated in suspension is added last and, if necessary, milled until the desired particle size and distribution is obtained. The particle size should not be so fine that the initial (24 hour) viscosity exceeds 30,000 cps at room temperature. Although the average diameter particle size of the water-soluble solid material can be from about 0.5 microns to about 500 microns, the particle diameter will preferably be from about 30 to about 200 microns, and most preferably from about 80 microns to about 120 microns.

To determine the stability of the concentrates of this invention, a storage stability program was conducted on numerous suspension concentrate samples over time. The samples were initially measured for viscosity and percent syneresis after 24 hours.

The viscosity measurements were made using a Brookfield Rheometer (Model DV III) and a Brookfield SC4-25 spindle set. The viscometer was run for 30 seconds at each selected speed, the readings were recorded for each, and the twelve digital readings averaged. Initial viscosities were measured after 24 hours. An acceptable initial viscosity range at room temperature was from about 100 to 30,000 cps.

After the viscosity profile was complete, a small glass rod was carefully submerged to the bottom center of the jar. The resistance of the glass rod in penetrating through the sample was subjectively evaluated for the degree of compacting. Any caking or claying was detected by simply inverting the sample container and noting the presence of material which does not come off the bottom of the container within thirty (30) seconds.

The processes of the present invention were demonstrated in detail in the following non-limiting working examples wherein all parts and percentages are by weight unless otherwise indicated.

EXAMPLE I

Diethylene glycol (255.0 gms) was mixed in a beaker (600 ml) together with a trystyryl phenol ethoxylate (13.8 gms); a surfactant such as disodium dodecyl diphenyl oxide disulfonate (7.2 gms) and an ethylene oxide/propylene oxide block copolymer (9.0 gms) at 25° C. using an Arde Barinco CJ-4 homogenizer at approximately 40% of the maximum power setting in the downward flow mode. The temperature of the mixture was raised due to the blending alone. When the temperature of the mixture reached 45–50° C., a hydroxypropyl ether guar gum derivative (15 gms) was added slowly in equal portions to the vortex of the mixture. Blending continued until the temperature of the mixture reached approximately 60–65° C. at which time the mixing direction of the homogenizer was reversed and the mixture circulated at 15–20% maximum power in the upward flow mode. At this point, the temperature of the mixture declined and when it reached approximately 55° C. the mixture was transferred to a low speed over-head mixer with a propeller blade. Low speed mixing continued until the mixture temperature dropped to about 25° C. at which point the mixture was placed in a HDPE jar for storage.

EXAMPLE 2

The procedure of example 1 was repeated and a non-aqueous suspension concentrate was prepared using the following ingredients in their respective amounts:

a) Polyethylene glycol (225 gms).

b) Tristyrylphenol ethoxylate (14.1 gms).

c) Disodium dodecyl diphenyl oxide disulfonate (9.9 gms).

d) Ethylene oxide/propylene oxide block copolymer (6.0 gms)

e) Hydroxypropyl ether guar gum (45 gms).

EXAMPLE 3

The procedure of example 1 was repeated and a non-aqueous suspension concentrate was prepared using the following ingredients in their respective amounts:

a) Diethylene glycol (225 gms).

b) Tristyrylphenol ethoxylate (13.8 gms).

c) Disodium dodecyl diphenyl oxide disulfonate (9.0 gms).

d) Ethylene oxide/propylene oxide block co-polymer (7.2 gms).

e) Hydroxypropyl ether guar gum (45 gms).

EXAMPLE 4

The procedure of example 1 was repeated and a non-aqueous suspension concentrate was prepared using the following ingredients in their respective amounts:

a) Triethylene glycol (210 gms).

b) Tristyrylphenol ethoxylate (13.8 gms).

c) Disodium dodecyl diphenyl oxide disulfonate (9.6 gms).

d) Ethylene oxide/propylene oxide block co-polymer (6.6 gms).

e) Hydroxypropyl ether guar gum (60 gms).

EXAMPLE 5

The procedure of example 1 was repeated and a non-aqueous suspension concentrate was prepared using the following ingredients in their respective amounts:

a) Diethylene glycol (225 gms).

b) Tristyrylphenol ethoxylate (13.8 gms).

c) Disodium dodecyl diphenyl oxide disulfonate (9.0 gms)

d) Ethylene oxide/propylene oxide block co-polymer (7.2 gms).

e) Xanthan gum (45 gms).

EXAMPLE 6

The procedure of example 1 was repeated and a non-aqueous suspension concentrate was prepared using the following ingredients in their respective amounts:

a) Polyethylene glycol (255 gms).

b) Tristyrylphenol ethoxylate (13.8 gms).

c) Disodium dodecyl diphenyl oxide disulfonate (6.0 gms)

d) Ethylene oxide/propylene oxide block co-polymer (10.2 gms).

e) Hydroxypropyl ether guar gum (15.0 gms).

EXAMPLE 7

The non-aqueous suspension concentrates prepared in examples 1–6 were then tested as to their syneresis and viscosity characteristics. Syneresis measurements were made using sealed, de-aerated samples that have been stored for 24 hours at room temperature (23–30° C.) and the value derived was expressed as a percentage defined by the ratio of the amount of bleed layer depth/total depth. An acceptable result is realized if the percent syneresis is equal to or less than thirty (30) percent after twenty-four (24) hours storage at 24° C. and thereafter less than five percent is visible after thirty (30) complete inversions of the storage jar.

Viscosity measurements were made using a Brookfield DV-III Rheometer equipped with a small sample adapter. The viscosity of the sample formulations (1–6) was measured at room temperature (23–30° C.) using a SC4-25 spindle running a geometric program cycle of 50 rpm to 100 rpm to 50 rpm with 5 rpm spindle speed increments at 30 second intervals throughout the cycle. The values reported below were obtained the midpoint of the geometric program cycle (100 rpm).

| Example | Syneresis | Viscosity |
|---------|-----------|-----------|
| 1 | 18.0% | 110 cPs |
| 2 | <5.0% | 993 cPs |
| 3 | 16.0% | 269 cPs |
| 4 | 13.0% | 499 cPs |
| 5 | 18.0% | 240 cPs |
| 6 | <5.0% | 370 cPs |

As expected, the syneresis and viscosity values show that the non-aqueous, water soluble suspension concentrates provide a storage and delivery medium for bioactive compounds that is viscous, yet does not readily separate into its separate continuous and discontinuous phases. This enables for the preparation of concentrated fertilizer, pesticide, herbicide and other agricultural or bioactive compositions that are highly concentrated, stable and thereby convenient to store and transport. The non-aqueous bioactive concentrates are also readily dispersible for easy mixing and dissolution in water at the users site.

What is claimed is:

1. A non-aqueous suspension concentrate comprising:
   a) from about 5.0 wt. % to about 85 wt. % of a water soluble active compound having a water solubility of no more than about 1.0 percent;
   b) from about 45 wt. % to about 90 wt. % of a non-aqueous water soluble carrier and;
   c) from about 4.0 wt. % to about 15 wt. % of a surfactant blend consisting essentially of:
      i) from about 0.1 wt. % to about 20 wt. % of at least one nonionic viscosity modifier;
      ii) from about 1.0 wt. % to about 20 wt. % of an anionic surfactant;
      iii) from about 0.1 wt. % to about 20 wt. % of at least one bulky non-ionic surfactant; and
   d) from about 5.0 wt. % to about 50 wt. % of a water hydratable polysaccharide.

2. The non-aqueous suspension concentrate of claim 1 wherein said water soluble active is a pesticide selected from the group consisting of microbiocides, herbicides, fertilizers, fungicides and mixtures thereof.

3. The non-aqueous suspension concentrate of claim 2 wherein said polysaccharide is selected from the group consisting of guar gum, gum arabic, xanthan gum, acacia gum, whelan gum, the hydroxy propyl ether, carboxymethyl ether or methyl ether derivatives thereof and mixtures thereof.

4. The non-aqueous concentrate of claim 3 wherein said non-aqueous, water-soluble carrier is selected from the group consisting of mono- and poly-functional ketones, water miscible ketones, formamide, dimethyl formamide, alkoxylates, dimethyl sulfoxide, N-methyl pyrrolidone, furfuryl, furfuryl alcohol, fatty acids, ethylene glycol, di- and tri-ethylene glycol, propylene glycol and mixtures thereof.

5. The concentrate of claim 4 wherein said nonionic viscosity modifier is selected from the group consisting of polyacrylic acids and the sodium salts thereof, polyalkylene oxide block copolymers and mixtures thereof.

6. The concentrate of claim 5 wherein the anionic surfactant is selected from the group consisting of:
   a) alkyl or alkyl ether sulfates of the formula R—O—SO$_3$—M or R—O—(C$_2$H$_4$O)$_x$—SO$_3$—M respectively; wherein R is an alkyl, alkenyl or alkylaryl group of about 8 to about 22 carbon atoms, x is a number of from 1 to 10, and M is a water-soluble cation;
   b) water-soluble salts of the formula R$_1$—SO$_3$—M wherein R$_1$ is selected from the group consisting of:
      i) a straight or branched chain, saturated aliphatic hydrocarbon radical having from about 8 to 24 carbon atoms;
      ii) a mono-, di-, or tri- C$_1$–C$_6$ alkyl substituted aryl wherein the aryl is a phenyl or naphthyl group;
      iii) alpha-olefins having from about 12 to 24 carbon atoms; and
      iv) naphthalene-formaldehyde condensation products;
   c) isethionates;
   d) n-methyl taurates;
   e) sulfosuccinates;
   f) sulfosuccinamates;
   g) β-alkyloxy alkane sulfonates;
   h) disulfonates; and
   i) mixtures thereof.

7. The non-aqueous suspension concentrate of claim 6 wherein said bulky nonionic surfactant is selected from the group consisting of at least one poly-oxyethyleneated and/or oxy-propyleneated poly(1-phenyethyl) phenol and phenyl ester of the formula:

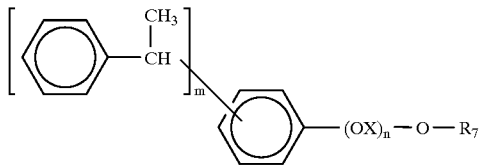

wherein:
   m is 2 or 3; (OX) is a recurring oxy ethylenated and/or oxy propylenated unit; n is a number of from about 12 to 35; and R$_7$ is a hydrogen, phosphate or sulfate entity.

8. The non-aqueous suspension concentrate of claim 7 wherein the nonionic viscosity modifier further comprises the polyglycol ethers of fatty alcohols, or polypropylene oxide condensation products and mixtures thereof, ethoxylated alkyl phenols, ethoxylated aliphatic alcohols, alkyl polyether alcohols, ethoxylated fatty acids, polyoxyethylene fatty acid esters, ethoxylated anhydrosorbitol esters, polyethylene sorbitan fatty acid esters, long chain amine and cyclic amine oxides, long chain tertiary phosphine oxides, long chain dialkyl sulfoxides and mixtures thereof.

9. The non-aqueous suspension concentrate of claim 8 wherein said water soluble active compound comprises from about 20 wt. % to about 60 wt. % of said suspension concentrate.

10. The non-aqueous suspension concentrate of claim 9 wherein said water soluble, non-aqueous carrier comprises from about 10 wt. % to about 85 wt. % of said suspension concentrate.

11. The non-aqueous suspension concentrate of claim 10 wherein said surfactant blend comprises from about 4.0 wt. % to about 15.0 wt. % of the suspension concentrate.

12. The non-aqueous suspension concentrate of claim 11 wherein said fertilizer is selected from the group consisting of potassium nitrate, ammonium dihydrophosphate, ammonium nitrate, sodium nitrate ammonium phosphate, ammonium polyphosphate, potassium hydrogen phosphate, disodium hydrogen phosphate, urea, and mixtures thereof.

13. The non-aqueous suspension concentrate of claim 11 wherein said pesticide is selected from the group consisting of boric acid, butocarboxime, acephate, dimethoate, dimehypo, vamidothion, methomyl and mixtures thereof.

14. The non-aqueous suspension concentrate of claim 11 wherein said herbicide is selected from the group consisting of dalapon (2,2 dichloropropirionic acid, sodium salt) ammonium sulfamate, dicamba, cacodylic acid, fomesafen; glyphosate and mixtures thereof.

15. The non-aqueous suspension concentrate of claim 11 wherein said fungicide is selected from the group consisting of copper sulfate, fosetyl-Al aluminum tris (O-ethyl phosphonate), benalaxyl, guazatine, kasugamycin and mixtures thereof.

* * * * *